United States Patent
Kerb et al.

[11] 4,056,633
[45] Nov. 1, 1977

[54] D-HOMO-20-KETOPREGNANES AND METHOD FOR INDUCING ANESTHESIA OR NARCOSIS

[75] Inventors: Ulrich Kerb; Rudolf Wiechert; Helmut Wachtel; Otto Engelfried; Klaus Kieslich, all of Berlin, Germany

[73] Assignee: Schering Aktiengesellschaft, Berlin and Bergkamen, Germany

[21] Appl. No.: 641,602

[22] Filed: Dec. 17, 1975

[30] Foreign Application Priority Data

Dec. 23, 1974 Germany ............................. 2461312
Feb. 14, 1975 Germany ............................. 2506688

[51] Int. Cl.² ....................... C01B 33/24; C07J 63/00
[52] U.S. Cl. ............................... 424/331; 260/586 C; 260/349; 260/455 R; 260/454; 260/464; 260/573; 544/58
[58] Field of Search ................. 260/349, 397.3, 397.4, 260/397.45, 586 E; 424/238

[56] References Cited
U.S. PATENT DOCUMENTS

3,876,705  4/1975  Valenta ............................. 260/586 E

*Primary Examiner*—Henry R. Jiles
*Assistant Examiner*—Cary Owens
*Attorney, Agent, or Firm*—Millen & White

[57] ABSTRACT

D-homo-20-ketopregnanes of the formula

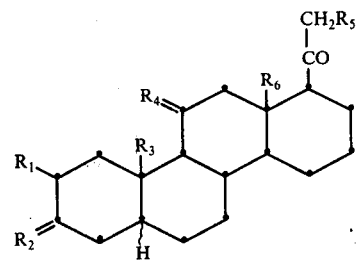

wherein $R_1$ is hydrogen, fluorine, chlorine, bromine, alkyl, alkoxy, or azido;

$R_2$ is oxygen,

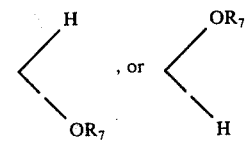

and $R_7$ is hydrogen, lower alkyl, or acyl of up to 5 carbon atoms;

$R_3$ is hydrogen or methyl $R_4$ is oxygen, two hydrogens,

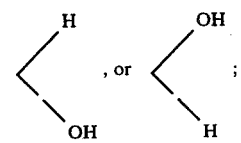

$R_5$ is hydrogen, hydroxy, alkoxy, azido, mercapto, thiocyano, cyano, dialkylamino, morpholino, thiomorpholino, or piperazino;

$R_6$ is methyl or ethyl;

the hydrogen atom in the 5-position is of the α- or β-configuration;

and acid addition salts thereof, possess narcotic-anesthetic activity.

37 Claims, No Drawings

D-HOMO-20-KETOPREGNANES AND METHOD FOR INDUCING ANESTHESIA OR NARCOSIS

BACKGROUND OF THE INVENTION

This invention relates to anesthetic-narcotic D-homo-20-ketopregnane derivatives.

Several steroid compounds, especially those of the pregnane series are known to have a central nervous-system depressant, anesthetic-narcotic effect and exert an influence on membrane permeability (J. A. Sutton, Postgrad. Med. J., 48 Suppl. 2 [1972]).

The novel D-homo-20-ketopregnanes of this invention, compared to the conventional steroids of the pregnane series, have a surprisingly brief induction time and high effectiveness. Thus, for example, 3α-hydroxy-D-homo-5α-20-one and 3α-hydroxy-D-homo-19-nor-5β-pregnan-20-one are five times more effective one minute after injection that the known sodium 21-hydroxy-5β-pregnane-3,20-dione-21-hemisuccinate.

2β-Ethoxy-3α-hydroxy-D-homo5α-pregnane-11,20-dione is twice as effective as the known substance. 2β-Azido-3α-hydroxy-D-homo-5α-pregnane-11,20-dione, although having the same effectiveness as the known substance, is distinguished by an exceedingly rapid onset of activity.

SUMMARY OF THE INVENTION

In a compositional aspect, this invention relates to D-homo-20-ketopregnane compounds of Formula I

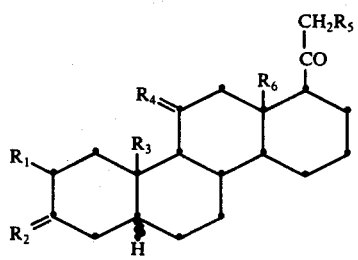

wherein $R_1$ is hydrogen, fluorine, chlorine, bromine, alkyl of 1-15 carbon atoms, alkoxy of 1-15 carbon atoms, or azido;

$R_2$ is oxygen,

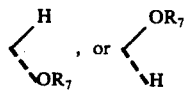

and $R_7$ is hydrogen, alkyl of 1-8 carbon atoms or alkanoyl of up to 5 carbon atoms;

$R_3$ is hydrogen or methyl'

$R_4$ is oxygen; two hydrogens,

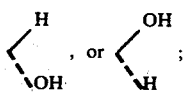

$R_5$ is hydrogen, hydroxy, alkoxy of 1-15 carbon atoms, mercapto, thioacetoxy, thiopropoxy, cyano, dialkylamino of 1-4 carbon atoms per alkyl, morpholino, thiomorpholino, or piperazino;

$R_6$ is methyl or ethyl;

the hydrogen atom in the 5-position is in the α- or β-configuration;

and pharmaceutically acceptable acid addition salts thereof.

In another compositional aspect, this invention relates to narcotic-anesthetic compositions comprising a narcotic-anesthetic amount per unit dosage of a compound of Formula I, in admixture with a pharmaceutically acceptable carrier.

In a process aspect, this invention relates to a method for inducing narcosis or anesthesia in human or veterinary medicine comprising administering to a patient a narcotic-anesthetic unit dosage amount of a compound of Formula I, or an acid addition salt thereof, in admixture with a pharmaceutically acceptable carrier.

DETAILED DESCRIPTION

Alkyl and alkoxy are those derived from straight-chain or branched-chain alkanes of up to 15 carbon atoms. Preferred are those of up to 8 carbon atoms. Examples include methyl, ethyl, propyl, isopropyl, n-butyl, tert.-butyl, isobutyl, n-pentyl, 1-methylbutyl, 2-methylbutyl, 3-methylbutyl, tert.pentyl, neopentyl, and the corresponding alkoxy groups, e.g., methoxy, ethoxy, propoxy, isobutoxy and n-pentoxy.

Lower alkyl means aliphatic residues derived from straight- or branched-chain alkanes of up to 6 carbon atoms, preferably those of 1-4 carbon atoms, as above.

Dialkylamino groups are those whose alkyl groups are of 1-4 carbon atoms, including those wherein the alkyl groups on the nitrogen atom are different. Examples are those wherein alkyl are methyl, ethyl and isobutyl incorporated in, e.g., dimethylamino-, diethylamino, ethylmethylamino-, dipropylamino-, butyl ethylamino-, groups.

Lower acyl is preferably alkanoyl of up to 5 carbon atoms, e.g., acetyl, propionyl, butyryl, and isobutyryl. Contemplated as equivalents are those of higher carbon atom content and of aryl, aralkyl, cycloalkanoyl and other organic carboxylic acids.

Acid addition salts are derived from acids which are pharmacologically and pharmaceutically acceptable. Examples include lactic acid, citric acid, hydrochloric acid, phosphoric acid, ascorbic acid, succinic acid, and maleic acid.

Examples of classes of compounds embraced by Formula I, and their acid addition salts, are those wherein:
a. $R_1$ is hydrogen;
b. $R_1$ is halogen;
c. $R_1$ is alkyl, preferably methyl;
d. $R_1$ is alkoxy, preferably methoxy;
e. $R_1$ is azido;
f. $R_2$ is oxygen, including those of (a) - (e), inclusive;
g. $R_2$ is

including those of (a) - (e), inclusive;
h. $R_4$ is oxygen, including those of (a) - (g), inclusive;
i. $R_4$ is two hydrogens, including those of (a) - (g), inclusive;
j. $R_4$ is

including those of (a) – (g), inclusive;

k. the 5-hydrogen is of the β-configuration, including those of (a) – (j), inclusive;

l. the 5-hydrogen is of the α-configuration, including those of (a) – (j), inclusive;

m. $R_5$ is hydrogen, including those of (a) – (l), inclusive;

n. $R_5$ is hydroxy, including those of (a) – (l), inclusive;

o. $R_5$ is alkoxy, including those of (a) – (l), inclusive;

p. $R_5$ is azido, including those of (a) –(l), inclusive;

q. $R_5$ is mercapto, including those of (a) – (l), inclusive;

r. $R_5$ is thioacetoxy, including those of (a) –(l), inclusive;

s. $R_5$ is thiopropoxy, including those of (a) –(l), inclusive;

t. $R_5$ is thiocyano, including those of (a) – (l), inclusive;

u. $R_5$ is cyano, including those of (a) – (l), inclusive;

v. $R_5$ is dialkylamino, including those of (a) – (l), inclusive;

w. $R_5$ is morpholino, including those of (a) – (l), inclusive;

x. $R_5$ is thiomorpholino, including those of (a) – (l), inclusive; and y. $R_5$ is piperazino, including those of (a) – (l), inclusive.

Anesthetic activity was tested on male NMRI mice weighting 20 – 25 g. The steroid compounds were suspended at 10% strength in polyhydroxyethylated castor oil and administered intravenously with the addition of 0.9% NaCl solution in a randomized test. The injection volume was 10 ml. per kg. of body weight and was injected within 10 seconds. Directly after injection, the test animals were placed in the supine position on a heated plate (35° C.), and the loss of the righting reflex was evaluated. A loss of the righting reflex was judged present if the test animals could not right themselves within 30 seconds to the prone position with all four paws in contact with the ground. The evaluation was conducted by statistical probit analysis.

The compounds of this invention are especially suitable for the induction of narcosis, wherein anesthesia after induction of the narcotic state is maintained by an inhalation anesthetic, such as, for example, ether, halothane, laughing gas, etc. For various therapeutic or diagnostic operations, the anesthetic effect of the compounds of this invention is itself sufficient. The anesthetic activity can be maintained in this case by repeated or continuous administration. The compounds of this invention generally have minor undesired side effects, as compared to previously known steroidal anesthetics.

The anesthetics based on the compounds of this invention are formulated in accordance with the usual pharmaceutical practice with one or more carrier materials, solubilizers, or binders. These conventional excipients ae pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegatable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages. The preparations of the anesthetic compounds according to the present invention are generally administered intravenously, or in certain cases, intramuscularly, e.g., to children.

The D-homo-20-ketopregnanes of Formula I are used as anesthetics in human and veterinary medicine. A dosage of 0.1 – 5 mg./kg. body weight, administered intravenously, is the dosage for an average person. The preferred dosages range from 0.2 to 2 mg./kg. The dosage depends on the physical condition of the patient and the degree and duration of the desired narcotic effect. It is possible by varying the dose to attain periods of narcosis of 10 minutes up to one hour or more. If a longer period of narcosis is to be maintained, subsequent dosages can correspond to the first dose, or lower dosages can be used. However, continuous administration, for example, in an amount of 0.05 – 1 mg./kg./minute, can also be done.

If the anesthetic preparations are to be applied intramuscularly, higher dosages are generally required, at least twice as high as for intravenous application.

In a process aspect, this invention relates to a process for the preparation of D-homo-20-ketopregnanes of Formula I,

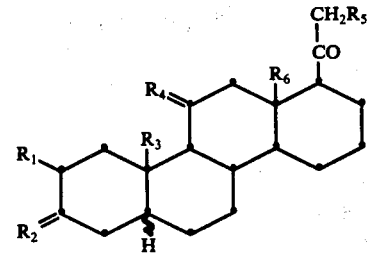

wherein an oxido-D-homopregnane of Formula II

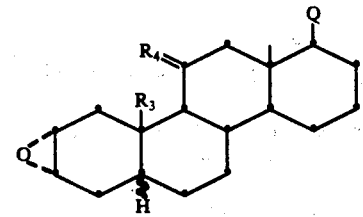

wherein $R_3$ and $R_4$ are as above; Q is

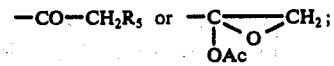

$R_5$ is as above and Ac is alkanoyl of 1–4 carbon atoms, preferably acetyl, is:

a. halogenated with a halogenating agent, preferably with a hydrogen halide or alkali metal halogenide, in an acidic solution;

b. alkoxylated with an alkanol in an acidic solution;

c. alkylated with lithium alkylidene in the presence of a Cu(I) salt;

d. converted to an azide using an alkali metal azide in an aprotic, water-miscible solvent; or e. after ketalization of the 20-keto group, reduced with lithium aluminum hydride in an ether, and the blocking group is cleaved off again.

In another process aspect, a formyloxy-D-homopregnane of Formula III

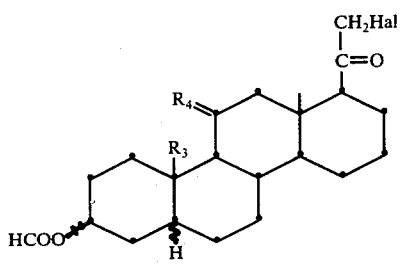

wherein $R_3$ and $R_4$ are as above and Hal is chlorine or bromine, a. is converted to an azide by reaction with a metal alkali azide in an aprotic, water-miscible solvent;

b. is converted to a cyano or thiocyano compound by reaction in a polar solvent;

c. is converted to a thioacyl compound by treatment with an alkali thioacylate and heating and is optionally saponified to the mercapto compound and the 3-formyl group is simultaneously split out;

d. is converted to a thioacylate by first splitting off the 3-formyl group and subsequently introducing a thioacylate residue by treatment with an alkali thioacylate and heating; or e. converted to an amine by first splitting off the 3-formyl group and then being reacted with an aliphatic or cycloaliphatic secondary amine, possibly further substituted by hetero atoms, and optionally converted by an acid to the acid addition salt.

In another process aspect, a $\Delta^{17}$-unsaturated D-homo steroid of Formula IV

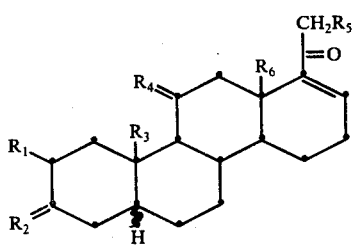

wherein $R_1$ and $R_5$ each are hydrogen and $R_2 - R_4$ and $R_6$ are as above, is catalytically hydrogenated in a convention manner. Conventionally, hydroxylation in the 11-position, and oxidation of the 11-hydroxy group or 3-hydroxy group to the corresponding keto group, or reduction of a 3-keto group to the 3-hydroxy group, and, if desired, inversion of the latter, can follow.

Halogenation at the 2-position of the 2,3-oxido steroids is effected by conventional methods. Preferred halogenating agents are either hydrogen halide, e.g., hydrogen fluoride, or alkali metal halogenides, e.g., lithium chloride, in the presence of an acid, e.g., acetic acid or perchloric acid. Suitable solvents are aprotic and protonic, water-miscible solvents, including tetrahydrofuran; dimethylformamide; alcohols; e.g., methanol or ethanol; dimethyl sulfoxide; and dioxane. The reaction is conducted in a temperature range of $-70°$ C. to $+50°$ C.

Alkoxylation at the 2-position is also done by conventional methods. An alkanol is reacted in the presence of a mineral acid catalyst which does not esterify the 2,3-oxido grouping, e.g., sulfuric acid or perchloric acid, at temperatures of 0°-60° C. The alkanol serves suitably as the solvent and can be used in any desired excess. Solubilizers, e.g., tetrahydrofuran or dioxane, can be added.

Alkylation at the 2-position is also done by conventional methods. Alkylation with lithium dialkyl copper is particularly preferred. Typically, 2 moles of lithium alkyl is reacted with one mole of copper(I) iodide in ether at low temperatures to produce a clear solution of lithium dialkyl cuprate, which is reacted in slight excess, preferably under an inert gas atmosphere, e.g., nitrogen or inert gas, with a 2,3-oxido steroid. Especially preferred solvents are ethers, e.g., diethyl ether, tetrahydrofuran and dioxane.

Introduction of an azido group into the 2-position is also done by conventional methods. A preferred method is treating a 2,3-oxido steroid with an alkali metal azide, such as lithium, sodium, or potassium azide, in a protonic or aprotic water-miscible solvent, optionally in the presence of aqueous acids, e.g., dilute acetic acid or perchloric acid, at an elevated temperature up to the boiling point of the reaction mixture.

Hydrogenation of the 2,3-oxido group in the presence of a 20-keto group is also done by conventional methods. It is necessary to block the 20-keto group, for example, by ketalization before the epoxide ring opening. Especially preferred is ketalization with an alkylene glycol, e.g., ethylene glycol, in the presence of an orthoformic acid alkyl ester and an acid catalyst, e.g., p-toluenesulfonic acid. The ketal can be used without further purification for the epoxide ring opening step, which is done with a strong reducing agent, such as lithium aluminum hydride. For this operation, the 20,20-alkylenedioxy-2,3-epoxy steroid is dissolved in an ether, e.g., diisopropyl ether, tetrahydrofuran, or dioxane, reducing agent is added and the mixture is heated. Subsequently, the blocking group is split off by treatment with an acid, for example, dilute sulfuric acid, at room temperature.

The substitution reactions at the 21-position are also conducted by conventional methods.

An azido group is introduced into the 21-position by reacting the 21-halogen steroid with an alkali azide, e.g., lithium, sodium, or potassium azide, in an aprotic, water-miscible solvent, e.g., tetrahydrofuran, acetonitrile or dimethylformamide, at temperatures of $-10°$ C. to $+50°$ C., preferably at room temperature.

The 3-formyloxy group is subsequently split off either by acidic hydrolysis with a dilute miner acid, e.g., hydrochloric acid/methanol, or by alkaline hydrolysis with a dilute base, for example, potassium hydroxide solution/methanol, with cooling. Use of an inert gas atmosphere is preferred.

Cyano or thiocyano groups are introduced at the 21-position by reacting a 21-halo steroid in a polar solvent, e.g., acetone, tetrahydrofuran, or an alcohol, e.g., methanol or ethanol, optionally with water present, with an alkali metal cyanide and/or thiocyanide, e.g., sodium cyanide or potassium rhodanide, at a temperature up to the boiling temperature of the reaction mixture. Under the foregoing conditions, the 3-formyl group is split off.

A thioacetyl group is introduced at the 21-position by dissolving a 21-halo steroid in a polar aprotic solvent, e.g., ketone, e.g., acetone or methyl isobutyl ketone; or an ether, e.g., tetrahydrofuran; dimethylformamide; dimethyl sulfoxide, etc., and treating with an alkali thioacylate. Temperatures between room temperature and the boiling temperature of the reaction mixture are used.

The formyl group in the 3-position can be split off before or after introduction of the acylthio group. The formyl group can be split off with beses and acids, but splitting with dilute acids, e.g., hydrogen chloride/methanol, is preferred.

Alternatively, the 21-thioacyl-3-formyloxy steroid can be converted, either directly or after acidic saponification to a 21-thioacyl-3-hydroxy steroid, with bases, e.g., potassium hydroxide/methanol, to a 21-mercapto-3-hydroxy steroid. This reaction preferably is done under a protective gas atmosphere at room temperature.

An amine group is introduced at the 21-position, by reacting a 21-halo-3-hydroxy steroid with the corresponding amine in an inert solvent at temperatures between 0° C. and the boiling temperature of the reaction mixture. Suitable inert solvents are those which do not react with the reactants, including hydrocarbons, e.g., hexane; aromatics, e.g., benzene; ketones, e.g., acetone; ether, e.g., tetrahydrofuran; acid derivatives, e.g., diethylformamide, etc.

Reduction of the $\Delta^{17}$-double bond is done with hydrogen in the presence of a catalyst customarily employed for hydrogenation of double bonds in steroids. Especially preferred are noble metal catalysts, e.g., platinum or palladium, optionally in a finely divided form on conventional carrier materials, including carbon, calcium carbonate, or strontium carbonate.

Suitable solvents are solvents inert to the reducing agent. Examples include alcohols, e.g., methanol or ethanol; ethers, e.g., tetrahydrofuran and dioxane; amides, e.g., dimethylformamide or diethylacetamide or mixtures thereof.

The reduction is done at temperatures of 0°–40° C., preferably at room temperature.

Introduction of a hydroxy group in the 11-position of steroids of Formula I is preferably done microbiologically by fermentation processes known to a person skilled in the art. A preferred method of 11α-hydroxylation is with strains of fungi of the genus Aspergillus, e.g., Aspergillus ochraceus.

If desired, the hydrogen group in the 3- or 11-position can be oxidized to the 3- or 11-keto group, respectively, by conventional methods. Suitable oxidizing agents include chromic acid in the form of the chromic acid-sulfuric acid complex (Jones reagent), chromic acid-pyridine complex, and chromic acid in aqueous acetic acid.

The Oppenauer oxidation with ketones/aluminum tri-tert.-butylate is also suitable. Other suitable methods include oxidation with N-bromoacetamide/tert.-butanol in aqueous pyridine and the oxidation with pyridine/sulfur trioxide complex in dimethyl sulfoxide/triethylamine.

The reduction of a 3-keto group optionally present to the 3-hydroxy group in the presence of an 11- and/or 20-keto group also is done by conventional methods.

Suitable reducing agents include complex metal hydrides, e.g., sodium borohydride in alcohol/water, dioxane/water, tetrahydrofuran/water, or pyridine/water solvents, or in the presence of sodium hydroxide solution; lithium tri-tert.-butoxyaluminum hydride in tetrahydrofuran at temperatures below room temperature; sodium trimethoxyborohydride in aqueous-methanolic sodium hydroxide solution; or hydrogen and Raney nickel catalyst at high pressures.

A preferred reduction method is using lithium tri-tert.-butoxyaluminum hydride in tetrahydrofuran at temperatures below room temperature. However, the reduction with triphenylphosphine in isopropanol in the presence of iridium tetrachoride is also suitable.

The 3-hydroxy compounds of Formula I can be present in the α- or β-configuration. These isomeric forms are optionally interconverted by conventional isomerization methods.

For example, 3α-hydroxy-D-homo-19-nor-5α-pregnan-20-one can be prepared from a 3β-hydroxy-D-homo-19-nor-5α-pregnane by way of an intermediate 3β-mesyloxy steroid, which is heated with lithium acetate and subsequently with potassium hydroxide solution.

A preferred isomerization procedure is exemplified by the reaction of 3β-hydroxy-D-homo-19-nor-5α-pregnanes with triphenylphosphine and formic acid in the presence of the diethyl azodicarboxylate to form 3α-formyloxy-D-homo-19-nor-5α-pregnane, which is saponified, for example, with methanolic potassium hydroxide solution, to a 3α-hydroxy-D-homo-19-nor-5α-pregnane.

However, a 3α-hydroxy-D-homo-19-nor-5β-pregnane can be oxidized by chromic acid to a 3-keto-D-homo-5β-pregnane, which is hydrogenated with Raney nickel under pressure and in the presence of a lower carboxylic acid to a corresponding 3β-hydroxy-D-homo-19-nor-5β-pregnane.

PREPARATION OF STARTING MATERIALS

The $\Delta^{17}$-unsaturated D-homo steroids used for the production of the compounds according to this invention can be prepared as follows:

Estran-17-ones are conventionally ethinylated (German Pat. No. 1,096,354; J. Org. Chem. 25 [1960] 1674; U.S. Pat. No. 3,084,173). The thus-obtained 17β-hydroxy-17α-ethinylestranes are converted in a known manner into the corresponding 16-dehydro steroids (German Unexamined Laid-Open Application DOS No. 1,593,521). After introduction of the 17-pregnane side chain in accordance with convention methods (Helv. 26 [1943] 1004; DOS No. 1,668,688), $\Delta^{16}$-19-nor-20-ketopregnanes are obtained, which are converted to the corresponding 16,17α-methylene steroids, for example, according to the method of Corey (E. J. Corey and M. Chaykovsky, J. Am. Chem. Soc. 84 [1962] 867; ibid. 84 [1962] 3782). Any $\Delta^4$-double bond present in the A-ring of the steroid molecule can be hydrogenated according to known methods, for example, with palladium or calcium carbonate in dimethylformamide, thus forming mixtures of the 5α-H- and 5β-H-isomers which can be readily separated from each other by the customary methods of preparative organic chemistry, such as chromatography and/or fractional crystallization. Finally, the $\Delta^{17}$-unsaturated D-homo steroids of Formula II are produced from the saturated 16,17α-methylene steroids in a conventional manner by ring expansion (DOS No. 1,135,903).

The following starting compounds were prepared in accordance with the above-mentioned reaction scheme:
1. 17β-hydroxy-3α-acetoxy-17α-ethinyl-5α-estrane; m.p. 90° C.

2. 17β-hydroxy-3α-acetoxy-17α-ethinyl-5β-estrane; m.p. 169° C.
3. 17β-hydroxy-3β-acetoxy-17α-ethinyl-5β-estrane; m.p. 141° C.
4. 3α-acetoxy-17-ethinyl-5α-estr-16-ene; $\epsilon_{228} = 10,500$ ($\epsilon_{234} = 9,290$)
5. 3β-acetoxy-17-ethinyl-5α-estr-16-ene; $\epsilon_{228} = 10,500$ ($\epsilon_{234} = 9,360$), m.p. 122° C.
6. 3α-acetoxy-17-ethinyl-5β-estr-16-ene; $\epsilon_{228} = 10,400$ ($\epsilon_{234} = 9,320$), m.p. 186° C.
7. 3β-acetoxy-17-ethinyl-5β-estr-16-ene; $\epsilon_{228} = 10,400$ ($\epsilon_{234} = 9,200$), m.p. 125° C.
8. 3α-acetoxy-19-nor-5α-pregn-16-en-20-one; $\epsilon_{240} = 9,320$, m.p. 148° C.
9. 3β-acetoxy-19-nor-5α-pregn-16-en-20-one; m.p. 159° C., $\epsilon_{239} = 9,400$
10. 3α-acetoxy-19-nor-5β-pregn-16-en-20one; $\epsilon_{239} = 9,220$, m.p. 98° C.
11. 3β-acetoxy-19-nor-5β-pregn-16-en-20-one; $\epsilon_{240} = 9,070$; m.p. 140° C.
12. 3α-hydroxy-16α,17-methylene-19-nor-5α-pregnan-20-one; m.p. 217° C.
13. 3α-acetoxy-16α,17-methylene-19-nor-5α-pregnan-20one; m.p. 128° C.
14. 3β-hydroxy-16α,17-methylene-19-nor-5α-pregnan-20-one; m.p. 210° C.
15. 3β-acetoxy-16α,17-methylene-19-nor-5α-pregnan-20-one; m.p. 185° C.
16. 3α-hydroxy-16α,17-methylene-19-nor-5β-pregnan-20-one; m.p. 152° C.
17. 3α-acetoxy-16α,17-methylene-19-nor-5β-pregnan-20-one; m.p. 102° C.
18. 3β-hydroxy-16α,17-methylene-19-nor-5β-pregnan-20-one; m.p. 162.5° C.
19. 3β-acetoxy-16α,17-methylene-19-nor-5β-pregnan-20-one; m.p. 154° C.
20. 3α-hydroxy-D-homo-19-nor-5α-pregn-17-en-20-one; $\epsilon_{233} = 9,080$, m.p. 217° C.
21. 3α-acetoxy-D-homo-19-nor-5α-pregn-17-en-20-one; $\epsilon_{233} = 9,210$, m.p. 153.5° C.
22. 3β-hydroxy-D-homo-19-nor-5α-pregn-17-en-20-one; $\epsilon_{230} = 8,870$, m.p. 187° C.
23. 3α-hydroxy-D-homo-19-nor-5β-pregn-17-en-20-one; $\epsilon_{233} = 9,060$, m.p. 166° C.
24. 3β-hydroxy-D-homo-19-nor-5β-pregn-17-en-20-one; $\epsilon_{232} = 9,020$
25. 19-norpregna-4,16-diene-3,20-dione; m.p. 176.5° C.
26. 16α,17-methylene-19-nor-4-pregnene-3,20-dione; m.p. 165.5° C.
27. 16α,17-methylene-19-nor-5α-pregnane-3,20-dione; m.p. 137° C.
28. 16α,17-methylene-19-nor-5β-pregnane-3,20-dione; m.p. 97.5° C.
29. D-homo-19-nor-5α-pregn-17-ene-3,20-dione; m.p. 172° C.
30. D-homo-19-nor-5β-pregn-17-ene-3,20-dione; m.p. 145.5° C. or 137° C.
31. 16α,17-methylene-18-methyl-19-nor-4-pregnene-3,20-dione; m.p. 130°-132° C.
32. 16α,17-methylene-18-methyl-19-nor-5α-pregnane-3,20-dione; m.p. 152°-153° C.
33. 16α,17-methylene-18-methyl-19-nor-5β-pregnane-3,20-dione; m.p. 134°-138° C.
34. 3α-hydroxy-16α,17-methylene-18-methyl-19-nor-5β-pregnan-20-one; m.p. 122°-123° C.
35. 3β-hydroxy-16α,17-methylene-18-methyl-19-nor-5β-pregnan-20-one; m.p. 110°-112° C.
36. 3α-hydroxy-16α,17-methylene-18-methyl-19-nor-5α-pregnan-20-one; m.p. 127°-128° C.
37. 3β-hydroxy-16α,17-methylene-18-methyl-19-nor-5α-pregnan-20-one; m.p. 105°-106° C.
38. 3α-hydroxy-18-methyl-D-homo-19-nor-5β-pregn-17-en-20-one; m.p. 127°-128° C.
39. 3β-hydroxy-18-methyl-D-homo-19-nor-5β-pregn-17-en-20-one; m.p. 151°-153° C.
40. 3α-hydroxy-18-methyl-D-homo-19-nor-5α-pregn-17-en-20-one; m.p. 141°-143° C.
41. 3β-hydroxy-18-methyl-D-homo-19-nor-5α-pregn-17-en-20-one; m.p. 117°-119° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

At −60° C., a solution of 3 g. of 2α,3α-epoxy-D-homo-5α-pregnan-20-one in 20 ml. of chloroform is added dropwise gradually to a mixture of 10 ml. of hydrogen fluoride, 13 ml. of tetrahydrofuran, and 6.5 ml. of chloroform. The reaction mixture is stirred for 2 hours at −30° C. Thereafter, the mixture is poured into potassium-bicarbonate-containing ice water, extracted with methylene chloride, washed neutral with water, and evaporated under vacuum. The residue is chromatographed on silica gel and recrstallized from ethyl acetate, thus obtaining 1.7 g. of 2β-fluoro-3α-hydroxy-D-homo-5α-pregnan-20-one, m.p. 171°-174° C.

The 2α,3α-epoxy-D-homo-5α-pregnan-20-one utilized as the starting material was prepared as follows:

A solution of 4.2 g. of 3β-hydroxy-D-homopregnane-5,17(17a)-dien-20-one in 500 ml. of methanol is hydrogenated in the presence of 900 mg. of palladium charcoal (10%) until the hydrogen absorption is terminated. The catalyst is filtered off and the solution is evaporated under vacuum. After recrystallization from methanol, 3.1 g. of 3β-hydroxy-D-homo-5α-pregnan-20-one is obtained, m.p. 190°-191° C.

A solution of 2.3 g. of 3β-hydroxy-D-homo-5α-pregnan-20-one in 20 ml. of pyridine is cooled to 0° C. and 1.15 ml of methane sulfochloride is added dropwise under stirring. The mixture is stirred for 30 minutes at 20° C., then precipitated by ice water; the thus-precipitated product is vacuum-filtered, taken up in methylene chloride, washed with water, and evaporated under vacuum. An analytical sample of 3β-mesyloxy-D-homo-5α-pregnan-20-one melts at 139°-140° C. after recrystallization from acetone.

15.2 g. of 3β-mesyloxy-D-homo-5α-pregnan-20-one is dissolved in 250 ml. of absolute benzene; 150 g. of neutral aluminum oxide is added thereto and the mixture agitated vigorously for 22 hours. Thereafter, the mixture is filtered, the filtrate is evaporated under vacuum, and the residue is recrystallized from methanol, thus obtaining 7.5 g. of D-homo-5α-pregn-2-en-20-one, m.p. 122°-123.5° C.

4.6 g. of D-homo-5α-pregn-2-en-20-one in 140 ml. of methylene chloride is combined with 4.6 g. of m-chloroperbenzoic acid and allowed to stand at 25° C. for 22 hours. Thereafter, the mixture is diluted with methylene chloride, washed with dilute sodium hydroxide solution and water, evaporated under vacuum, and the residue recrystallized from acetone/hexane, thus obtaining 3.2 g. of 2α,3α-epoxy-D-homo-5α-pregnan-20-one, m.p. 133°–135° C.

EXAMPLE 2

1.1 g. of 2α,3α-epoxy-D-homo-5α-pregnan-20-one is agitated with 3.3 g. of lithium chloride in 20 ml. of acetic acid for 22 hours at room temperature. After precipitation into water, the reaction mixture is vacuum-filtered; the precipitate is vacuum-filtered and taken up in methylene chloride. The methylene chloride solution is evaporated under vacuum, and the residue is recrystallized from acetone/hexane. The thus-produced 2β-chloro-3α-hydroxy-D-homo-5α-pregnan-20-one melts at 167°–170° C.

EXAMPLE 3

As described in Example 2, 2β-bromo-3α-hydroxy-D-homo-5α-pregnan-20-one is obtained from 2α,3α-epoxy-D-homo-5α-pregnan-20-one with lithium bromide in acetic acid. Melting point of the product: 141° C. (decomposition).

EXAMPLE 4

500 mg. of 2α,3α-epoxy-D-homo-5α-pregnan-20-one is agitated in 40 ml. of methanol with 0.5 ml. of 70% perchloric acid for 1 hour at 25° C. Thereafter, the mixture is stirred into an aqueous potassium bicarbonate solution and extracted with ethyl acetate. The extract is washed with water, dried, and evaporated under vacuum. Recrystallization from acetone/hexane yields 310 mg. of 3α-hydroxy-2β-methoxy-D-homo-5α-pregnan-20-one, m.p. 156°–158° C.

EXAMPLE 5

500 mg. of 2α,3α-epoxy-D-homo-5α-pregnan-20-one is agitated in 60 ml. of n-butanol with 0.6 ml. of concentrated sulfuric acid for 16 hours at 25° C. After working up the reaction mixture as described in Example 4, 295 mg. of 2β-butoxy-3α-hydroxy-D-homo-5α-pregnan-20-one is obtained, m.p. 107°–110° C.

EXAMPLE 6

At −40° C., 86 ml. of an ethereal methyl lithium solution (0.126 mole) is added dropwise under argon to a suspension of 12 g. of copper(I) iodide (0.063 mole) in 30 ml. of ether. Thereafter, a solution of 12 g. of 2α,3α-epoxy-D-homo-5α-pregnane-11,20-dione in 75 ml. of tetrahydrofuran and 75 ml. of ether is gradually added dropwise, so that the internal temperature does not rise above −20° C. The reaction mixture is agitated for 30 hours at −20° C., combined with aqueous ammonium chloride solution, and diluted with ethyl acetate. The organic phase is separated, washed with water, and evaporated. The residue is chromatographed on silica gel, and the thus-separated 3α-hydroxy-2β-methyl-D-homo-5α-pregnane-11,20-dione (7.1 g.) is recrystallized from methylene chloride/isopropyl ether, m.p. 173°–175° C.

The 2α,3α-epoxy-D-homo-5α-pregnane-11,20-dione used as the starting material was prepared as follows:

17.7 g. of 3β-hydroxy-D-homo-5α-pregnane-11,20-dione are dissolved in 170 ml. of pyridine, cooled to 0°–5° C., combined with 8.5 ml. of methanesulfochloride, and stirred for 30 minutes at room temperature. Thereafter, the mixture is precipitated into ice water; the product is vacuum-filtered, washed with water, and dried, thus obtaining 22 g. of 3β-mesyloxy-D-homo-5α-pregnane-11,20-dione, m.p. 149°–149.5° C. (decomposition).

21.9 g. of mesylate is stirred in 500 ml. of benzene with 250 g. of neutral aluminum oxide for 18 hours at room temperature. The mixture is filtered off from the aluminum oxide, and the filtrate is concentrated by evaporation. Yield: 16.2 g. of D-homo-5α-pregn-2-ene-11,20-dione (m.p. 165°–169° C.).

11.2 g. of D-homo-5α-pregn-2-ene-11,20-dione is combined in 200 ml. of methylene chloride with 11 g. of m-chloroperbenzoic acid and stirred for 30 minutes at room temperature. Thereafter, the mixture is diluted with methylene chloride, washed with 2N sodium hydroxide solution and water, evaporated, and the residue chromatographed on silica gel. After crystallization from methylene chloride/methanol, 8.4 g. of 2α,3α-epoxy-D-homo-5α-pregnane-11,20-dione is obtained, m.p. 206°–207° C.

At −30° C., 820 mg. of 2α,3α-epoxy-D-homo-5α-pregnane-11,20-dione in 25 ml. of tetrahydrofuran is added dropwise to a di-n-butyl lithium cuprate solution (prepared from 29 millimoles of n-butyl lithium and 14.5 millimoles of copper(I) iodide in 50 ml. of ether); the mixture is agitated under argon for 48 hours at 0°–5° C. After the mixture is worked up as described in Example 6, 250 mg. of 2β-n-butyl-3α-hydroxy-D-homo-5α-pregnane-11,20-dione is obtained, m.p. 132°–134° C.

EXAMPLE 8

10 g. of 2α,3α-epoxy-D-homo-5α-pregnane-11,20-dione is dissolved in 200 ml. of dimethylformamide; a solution of 11.5 g. of sodium azide in 65 ml. of water is added thereto, and the mixture is stirred for 5 hours under nitrogen at 110° C. Thereafter, the mixture is poured into an ice-cold sodium chloride solution; the thus-precipitated product is vacuumfiltered, washed with water, and dried. Recrystallization from acetone/hexane yields 5.2 g. of 2β-azido-3α-hydroxy-D-homo-5α-pregnane-11,20-dione, m.p. 132°–135° C.

EXAMPLE 9

20 Grams of 20-acetoxy-3α-formyloxy-D-homo-5α-pregn-20-en-11-one are dissolved in 500 ml. of carbon tetrachloride and 5 ml. of epichlorhydrin are added. The reaction mixture is cooled down to 0° C. and 2.7 ml. of bromine in 20 ml. of carbon tetrachloride are added dropwise. Then the reaction mixture is diluted with methylene chloride, washed with aqueous solutions of sodium acetate and sodium hydrogen sulfite and then with water and concentrated under vacuum. There is obtained 21.5 g. 21-bromo-3α-formyloxy-D-homo5α-pregnan-11,20-dione.

Two grams of 21-bromo-3α-formyloxy-D-homo-5α-pregnane-11,20-dione in 150 ml. of ethanol and 15 ml. of water is combined with 1 g. of potassium cyanide and refluxed for 1 hour. Thereafter, the mixture is stirred into ice water, acidified with dilute sulfuric acid, and extracted with methylene chloride. The methylene chloride extract is washed with water, dried over sodium sulfate, and evaporated. After recrystallization from acetone/hexane, 910 mg. of 21-cyano-3α-hydroxy-D-homo-5α-pregane-11,20-dione is obtained, m.p. 173°–175° C.

The 21-bromo-3α-formyloxy-D-homo-5α-pregnane-11,20-dione employed as the starting material is prepared as follows:

80 g. of 3α-formyloxy-D-homo-5α-pregnane-11,20-dione is dissolved in 800 ml. of benzene and 500 ml. of isopropenyl acetate. After addition of 6 ml. of concentrated sulfuric acid, the mixture is gradually distilled over 9 hours. Thereafter, the mixture is diluted with benzene, washed with sodium bicarbonate solution and water, and evaporated. The residue is chromatographed on silica gel; the 20-enolacetate is eluted with hexane-/acetone (9 : 1) and recrystallized on methylene chloride/isopropyl ether, thus obtaining 56 g. of 20-acetoxy-3α-formyloxy-D-homo-5α-pregn-20-en-11-one, m.p. 151°-154° C.

EXAMPLE 10

4 g. of 21-bromo-3α-formyloxy-D-homo-5α-pregnane-11,20-dione is heated to the boiling point in 150 ml. of acetone with 4 g. of potassium thioacetate for 1 hour under nitrogen. The mixture is then precipitated into ice water, extracted with methylene chloride, and washed with water. The methylene chloride extract is evaporated under vacuum, and the residue is chromatographed. Recrystallization from acetone/hexane yields 1.3 g. of 21-acetylthio-3α-formyloxy-D-homo-5α-pregnane-11,20-dione, m.p. 171°-175° C.

EXAMPLE 11

500 mg. of 21-acethylthio-3α-formyloxy-D-homo-5α-pregnane-11,20-dione is agitated in 10 ml. of methanol and 10 ml. of methylene chloride with 200 mg. of potassium hydroxide for 45 minutes under argon. After acidifying with acetic acid, the mixture is taken up in methylene chloride, washed with water, and the solvent evaporated under vacuum. The residue is purified by thin layer chromatography. After recrystallization from isopropyl ether/methylene chloride, 215 mg. of 21-mercapto-3α-hydroxy-D-homo-5α-pregnane-11,20-dione is obtained, m.p. 141°-143° C.

EXAMPLE 12

Two grams of 21-bromo-3α-formyloxy-D-homo-5α-pregnane-11,20-dione is stirred in 15 ml. of methylene chloride and 15 ml. of a 3% methanolic hydrogen chloride solution for 24 hours at 0°-5° C. The mixture is diluted with methylene chloride, washed with water, and the solvent is evaporated under vacuum. 1.7 g. of the thus-obtained 21-bromo-3α-hydroxy-D-homo-5α-pregnane-11,20-dione is agitated in 30 ml. of dimethylformamide with 2 g. of potassium thiopropionate for 5 hours at 60° C. After cooling, the mixture is poured into a sodium chloride solution; the thus-precipitated product is vacuum-filtered, dried, and recrystallized from acetone/hexane, thus obtaining 910 mg. of 21-propionylthio-3α-hydroxy-D-homo-5α-pregnane-11,20-dione, m.p. 115°-120° C.

EXAMPLE 13

One gram of 21-bromo-3α-hydroxy-D-homo-5α-pregnane-11,20-dione is stirred in 15 ml. of dimethylformamide with 1 g. of potassium thioacetate for 5 hours at 60° C. After the reaction mixture has been worked up as set forth in Example 12 and has been recrystallized from acetone/hexane, 430 mg. of 21-acetylthio-3α-hydroxy-D-home-5α-pregnane-11,20-dione is obtained, m.p. 148°-151° C.

EXAMPLE 14

500 mg. of 21-bromo-3α-formyloxy-D-homo-5α-pregnane-11,20-dione is dissolved in 10 ml. of dimethyl sulfoxide, combined with 600 mg. of sodium azide, and stirred for 20 minutes at room temperature. Thereafter, the mixture is stirred into ice water; the precipitated product is vacuum-filtered, washed with water, and dissolved in methylene chloride. The methylene chloride solution is evaporated and the residue triturated with pentane, thus obtaining 410 mg. of amorphous 21-azido-3α-formyloxy-D-homo-5α-pregnane-11,20-dione.

400 mg. of 21-azido-3α-formyloxy-D-homo-5α-pregnane11,20-dione is agitated in 5 ml. of methanol and 5 ml. of methylene chloride with 80 mg. of potassium hydroxide for 1 hour at 0°-5° C. under argon. The mixture is then neutralized with acetic acid, diluted with methylene chloride, washed with water, and evaporated under vacuum. Recrystallization from isopropyl ether/methylene chloride yields 210 mg. of 21-azido-3α-hydroxy-D-homo-5α-pregnane-11,20-dione, m.p. 153°-155° C.

EXAMPLE 15

5 g. of 20-acetoxy-2α,3α;20,21-bis-epoxy-D-homo-5α-pregnane is dissolved in 150 ml. of dimethylformamide; a solution of 25 g. sodium azide in 60 ml. of water is added thereto, and the mixture is stirred for 5 hours at 110° C. under nitrogen. Subsequently, the mixture is stirred into a sodium chloride solution, and acidifed with dilute sulfuric acid; the precipitated product is vacuum-filtered, washed with water, and dried. After recrystallization from acetone/hexane, 3.7 g. of 2β,21-diazido-3α-hydroxy-D-homo-5α-pregnan-20-one, m.p. 148°-151° C.

The 20-acetoxy-2α,3α;20,21-bis-epoxy-D-homo-5α-pregnane used as the starting material was prepared as follows:

20 g. of D-homo-5α-pregn-2-en-20-one is dissolved in 200 ml. of benzene and 125 ml. of isopropenyl acetate, combined with 1.5 ml. of concentrated sulfuric acid, and gradually distilled during 10 hours. The mixture is worked up and chromatographed as set forth in Example 9. Recrystallization from isopropyl ether yields 16 g. of 20-acetoxy-D-homo-5α-pregna-2,20-diene, m.p. 93°-95° C.

10 g. of 20-acetoxy-D-homo-5α-pregna-2,20-diene is combined in 300 ml. of ethylene chloride with 20 g. of p-nitroperbenzoic acid and stirred for 12 hours at room temperature. The mixture is then diluted with methylene chloride, then washed with ice-cold 5% sodium bisulfite solution and thereafter with sodium bicarbonate solution and water, dried, and evaporated under vacuum. Trituration with hexane yields 6.5 g. of amorphous 20-acetoxy-2α,3α;20,21-bis-epoxy-D-homo-5α-pregnane.

EXAMPLE 16

600 mg. of 20acetoxy-2α,3α;20,21-bis-epoxy-D-homo-5α-pregnane is stirred in 60 ml. of ethanol with 0.6 ml. of 70% perchloric acid for 1.5 hours at room temperature. The mixture is then poured into ice water; the precipitated product is vacuum-filtered, washed with water, and dried. Recrystallization from acetone/hexane yields 220 mg. of 2β,21-diethoxy-3α-hydroxy-D-homo-5α-pregnan-20-one, m.p. 139°-141° C.

EXAMPLE 17

700 mg. of 21-bromo-3α-hydroxy-D-homo-5α-pregnane-11,20-dione is stirred in 10 ml. of toluene and 10 ml. of morpholine for 16 hours at 25° C. The mixture is then evaporated under vacuum and taken up in ether; the ether solution is washed with water and concentrated. The residue is recrystallized from ether/ethanol, thus obtaining 385 mg. of 3α-hydroxy-21-morpholine-D-homo-5β-pregnane-11,20-dione, m.p. 173°–177° C.

EXAMPLE 18

1.2 g. of 21-bromo-3α-hydroxy-D-homo-5α-pregnane-11,20-dione is agitated in 100 ml. of toluene and 20 ml. of diethylamine for 20 hours at 25° C. Subsequently, the solution is evaporated under vacuum, taken up in ether, washed with water, and concentrated. After recrystallization from acetone/hexane, 510 mg. of 21-diethylamino-3α-hydroxy-D-homo-5α-pregnane-11,20-dione is obtained, m.p. 147°–151° C.

EXAMPLE 19

One gram of 21-bromo-3α-hydroxy-D-homo-5α-pregnane-11,20-dione is refluxed in 80 ml. of acetone containing 1 g. of potassium rhodanide for 3.5 hours. Thereafter, the mixture is concentrated under vacuum, precipitated with water, vacuum-filtered, washed with water, and dried. Recrystallization from acetone/hexane yields 320 mg. of 3α-hydroxy-21-thiocyanato-D-homo-5α-pregnane-11,20-dione, m.p. 122°–125° C.

EXAMPLE 20

50 g. of 2α,3α-epoxy-D-homo-5α-pregnan-20-one is dissolved in 500 ml. of ethylene glycol and 250 ml. of methylene chloride; 100 ml. of ethyl orthoformate and 500 mg. of p-toluenesulfonic acid are added to the reaction mixture. The latter is agitated for 24 hours at 25° C.; then, 1 ml. of pyridine is added thereto and the methylene chloride is distilled off under vacuum. The mixture is then poured into ice water. The precipitated product is vacuum filtered, washed with water, and dried under vacuum at 60° C. Yield: 55.6 g. of crude 20,20-ethylenedioxy-2α,3α-epoxy-D-homo-5α-pregnane which is further processed without any additional purification. 18.7 g. of this ketal is dissolved in 700 ml. of basic tetrahydrofuran; a solution of 8 g. of lithium aluminum hydride in 200 ml. of tetrahydrofuran is added dropwise, and the mixture is heated for one hour under reflux. Subsequently, 60 ml. of 3N sulfuric acid is added dropwise with ice cooling; the mixture is agitated for 5 hours at room temperature and poured into ice water. The thus-precipitated product is vacuum-filtered, taken up in methylene chloride, washed with water, and evaporated. The residue is recrystallized from methanol, thus obtaining 11.3 g. of 3α-hydroxy-D-homo-5α-pregnan-20-one, m.p. 162°–163° C.

EXAMPLE 21

400 mg. of 2α,3α-epoxy-D-homo-5α-pregnane-11,20-dione is combined in 5 ml. of absolute ethanol with 0.1 ml. of 70% perchloric acid and stirred for 10 minutes at room temperature. Subsequently, the mixture is stirred into an aqueous sodium chloride solution and extracted with methylene chloride. The methylene chloride solution is washed with water and evaporated. The residue is purified by layer chromatography. The product is 345 mg. of 2β-ethoxy-3α-hydroxy-D-homo-5α-pregnane-11,20-dione, m.p. 67°–68° C.

EXAMPLE 22

2.51 g. of D-homo-19-nor-5α-pregn-17-ene-3,20-dione is hydrogenated in 80 ml. of dimethylformamide in the presence of 0.25 g. of palladium on charcoal (5% strength) until 1 millimole of hydrogen has been absorbed per millimole of substance. The mixture is filtered off from the catalyst. The filtrate is concentrated under reduced pressure and poured into ice water. The precipitate is filtered off, washed with water, and taken up in methylene chloride. The methylene chloride solution is washed with water, dried, and evaporated. The residue is chromatographed on silica gel. After recrystallization from methylene chloride/hexane, the pure D-homo-19-nor-5α-pregnane-3,20-dione melts at 132°–135° C.

EXAMPLE 23

629 mg. of D-homo-19-nor-5β-pregn-17-ene-3,20-dione is hydrogenated and worked up analogously to Example 22. After chromatography on silica gel and preparative layer chromatography, 387 mg. of D-homo-19-nor-5β-pregnane-3,20-dione is obtained, m.p.108°–110° C.

EXAMPLE 24

1.1 g. of D-homo-3β-hydroxy-19-nor-5α-pregn-17-en-20-one is hydrogenated and worked up as Example 22. Preparative layer chromatography and recrystallization from methylene chloride/hexane yield 0.86 g. of 3β-hydroxy-D-homo-19-nor-5α-pregnan-20-one, m.p. 170°–172° C.

EXAMPLE 25

617 mg. of 3α-hydroxy-D-homo-19-nor-5β-pregn-17-en-20-one is hydrogenated as in Example 22 and worked up. After preparative layer chromatography and recrystallization from methylene chloride/hexane, 532 mg. of 3α-hydroxy-D-homo-19-nor-5β-pregnan-20-one is obtained, m.p. 114°–115° C.

EXAMPLE 26

240 mg. of 3α-hydroxy-D-homo-19-nor-5α-pregna-17-en-20-one is hydrogenated and worked up as in Example 22. Chromatography and recrystallization from acetone/hexane yield 3α-hydroxy-D-homo-19-nor-5α-pregnan-20-one.

EXAMPLE 27

0.9 g. of 3β-hydroxy-D-homo-19-nor-5β-pregn-17-en-20-one is hydrogenated and worked up as in Example 22. After chromatography and recrystallization from acetone/hexane, 3β-hydroxy-D-homo-19-nor-5β-pregnan-20-one is obtained.

EXAMPLE 28

3α-Hydroxy-18-methyl-D-homo-19-nor-5β-pregn-17-en-20-one is hydrogenated as given in Example 22. Recrystallization from acetone/hexane yields 3α-hydroxy-18-methyl-D-homo-19-nor-5β-pregnan-20-one, m.p. 104.5° –105° C.

EXAMPLE 29

A 20-liter glass fermentor is charged with 15 liters of a nutrient solution of 1% corn steep liquor and 1% soybean meal, sterilized by heating for one-half hour at 120° C., and after cooling inoculated with 250 ml. of a 3 day old shaken culture of Aspergillus ochraceus ATCC 1008. The shaken culture was produced by inoculating 250 ml. of the same medium with a supernatant broth of a 7 day old agar slant.

After incubation for 24 hours at 20° C. under agitation (220 r.p.m.) and aeration (15 l./min.), 1,8 l. of the thus-produced culture is withdrawn under sterile conditions and transferred into a 50-liter stainless steel fermentor filled with 28 l. of the same medium. After incubation for 12 hours, a sterile-filtered solution of 15 g. of D-homo-19-nor-5α-pregnane-3,20-dione in 150 ml. of dimethylformamide is added thereto. After another 32 hours of fermentation, the course of which is followed by the withdrawal of samples, the culture broth is filtered off over gauze. The mycelium residue is washed several times with water. The filtrate and the wash water are extracted with methyl isobutyl ketone. The combined extracts are concentrated in a forced circulation evaporator and evaporated to dryness under vacuum in a rotary evaporator. The residue is washed with 100 ml. of hot hexane to remove the defrother employed. In this way, 15.2 q. of a crude product is obtained. Chromatography on silica gel with a gradient elution of methylene chloride : methylene chloride/acetone (2 : 1) yields 11α-hydroxy-D-homo-19-nor-5α-pregnane-3,20-dione, which is recrystallized from ethyl acetate. Melting point: 152°–155° C.

EXAMPLE 30

Under the conditions of Example 29, 15 g. of D-homo-19-nor-5β-pregnane-3,20-dione is fermented with Aspergillus ochraceus ATCC 1008. Column chromatography on silica gel (gradient elution hexane/acetone) yields 11α-hydroxy-D-homo-19-nor-5β-pregnane-3,20-dione, which is recrystallized from ethyl acetate, m.p. 122°–124° C.

EXAMPLE 31

45 g. of 11α-hydroxy-D-homo-19-nor-5β-pregnane-3,20-dione is dissolved in 3.2 l. of acetone and 0.9 l. of methylene chloride and, with agitation and water cooling, 45 ml. of a chromic acid solution, produced from 26.72 g. of CrO₃ and 23 ml. of concentrated sulfuric acid, and brought with water to a volume of 100 ml., is added dropwise thereto so that the internal temperature does not rise above 20° C. The mixture is then stirred for 5 minutes, combined with 200 ml. of methanol, and buffered with sodium acetate. One-third of the solvent is distilled off under vacuum, and the remainder poured into ice water. The thus-precipitated product is vacuum-filtered, washed with water, dried, and chromatographed on silica gel. By gradient elution with hexane/5–30% acetone, 40 g. of D-homo-19-nor-5β-pregnane-3,11,20-trione is obtained which melts, after recrystallization from acetone/hexane, at 127°–129° C.

EXAMPLE 32

A solution of 23.5 g. of D-homo-19-nor-5β-pregnane-3,11,20-trione in 930 ml. of tetrahydrofuran is saturated with argon and cooled to −15° C. 37 g. of lithium tert.-butoxy-aluminum hydride is added to the reaction mixture. The latter is stirred for 15 minutes at −15° C. under argon and then poured into hydrochloric ice water. The thus-precipitated product is vacuum-filtered, washed with water, and dried. By recrystallization from isopropyl ether/methylene chloride, 14.5 g. of 3α-hydroxy-D-homo-19-nor-5β-pregnane-11,20-dione is obtained, m.p. 142° –143.5° C.

EXAMPLE 33

1.6 g. of D-homo-19-nor-5β-pregna-3,11,20-trione is hydrogenated in 45 ml. of glacial acetic acid after adding 3.5 g. of Raney nickel under a hydrogen pressure of 160 atm. gauge. The catalyst is filtered off and washed with methanol. The filtrate is stirred into ice water. The thus-precipitated product is vacuum-filtered, washed with water, dried, and chromatographed on silica gel. By elution with hexane/acetone (7 + 3), 920 mg. of 3β-hydroxy-D-homo-19-nor-5β-pregnane-11,20-dione is separated and recrystallized from isopropyl ether; m.p. 159°–161° C.

EXAMPLE 34

1.8 g. of 11α-hydroxy-D-homo-19-nor-5α-pregnane-3,20-dione is oxidized according to Example 31. After recrystallization from actone/hexane, 1.4 g. of D-homo-19-nor-5α-pregnane-3,11,20-trione is obtained, m.p. 141°–143° C.

EXAMPLE 35

1.2 g. of D-homo-19-nor-5α-pregnane-3,11,20-trione is reduced according to Example 32. By recrystallization from isopropyl ether/methylene chloride, 990 mg. of 3β-hydroxy-D-homo-19-nor-5α-pregnane-11,20-dione is obtained, m.p. 170°–172° C.

EXAMPLE 36 a. 1.03 g. of 3β-hydroxy-D-homo-19-nor-5α-pregnane-11,20-dione is dissolved in 20 ml. of tetrahydrofuran; 1.75 g. of triphenylphosphine and 0.23 ml. of formic acid are added thereto, and a solution of 1.01 ml. of the ethyl ester of azodicarboxylic acid in 10 ml. of tetrahydrofuran is added dropwise thereto. The reaction solution is then stirred for 20 minutes and poured into an ice-cold sodium chloride solution. The thus-precipitated product is vacuum-filtered, washed with water, and dried. Chromatograph on silica gel (gradient elution with methylene chloride/5–20% ethyl acetate) is used to isolate the amorphous 3α-formyloxy-D-homo-19-nor-5α-pregnane-11,20-dione. b. 800 mg. of this formate is dissolved in 8 ml. of methylene chloride and 8 ml. of methanol; 88 mg. of potassium hydroxide is added thereto, and the mixture is stirred for 15 minutes at 23° C. After neutralization with acetic acid, the mixture is evaporated under vacuum, dissolved in methylene chloride, washed with water, and concentrated. Crystallization from methylene chloride/isopropyl ether yields 465 mg. of 3α-hydroxy-D-homo-19-nor-5α-pregnane-11,20-dione, m.p. 157° – 158° C.

EXAMPLE 37

Analogously to Example 31, 4.5 g. of 3β-hydroxy-D-homo-19-nor-5α-pregnan-20-one is treated with 4.5 ml. of Jones reagent, worked up, and purified, thus obtaining 3.9 g. of D-homo-19-nor-5α-pregnane-3,20-dione, m.p. 132.5 ° – 133° C.

EXAMPLE 38

0.33 g. of 3β-hydroxy-18-methyl-D-homo-19-nor-5α-pregn-17(17a)-en-20-one is hydrogenated according to Example 22. Recrystallization from methylene chloride/hexane yields 0.28 g. of 3β-hydroxy-18-methyl-D-homo-19-nor-5α-pregnan-20-one, m.p. 156°–158° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A D-homo-20-ketopregnane of the formula

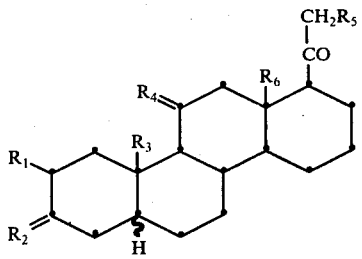

wherein $R_1$ is hydrogen, fluorine, chlorine, bromine, alkyl of 1-15 carbon atoms, alkoxy of 1-15 carbon atoms, or azido;

$R_2$ is oxygen

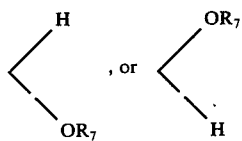

and $R_7$ is hydrogen, alkyl of 1-8 carbon atoms or alkanoyl of up to 5 carbon atoms;

$R_3$ is hydrogen or methyl;

$R_4$ is oxygen, two hydrogens,

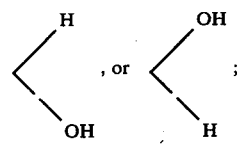

$R_5$ is hydrogen, hydroxy, alkoxy of 1-15 carbon atoms or mercapto, $R_6$ is methyl or ethyl;

the hydrogen atom in the 5-position is in the α-or β-configuration; and pharmaceutically acceptable acid addition salts thereof.

2. 2β-Fluoro-3α-hydroxy-D-homo-5α-pregnan-20-one, a compound of claim 1.

3. 2β-Chloro-3α-hydroxy-D-homo-5α-pregnan-20-one, a compound of claim 1.

4. 2β-Bromo-3α-hydroxy-D-homo-5α-pregnan-20-one, a compound of claim 1.

5. 3α-Hydroxy-2β-methoxy-D-homo-5α-pregnan-20-one, a compound of claim 1.

6. 2β-Butoxy-3α-hydroxy-D-homo-5α-pregnan-20-one, a compound of claim 1.

7. 3α-Hydroxy-2β-methyl-D-homo-5α-pregnane-11,20-dione, a compound of claim 1.

8. 2β-n-Butyl-3α-hydroxy-5α-pregnane-11,20-dione, a compound of claim 1.

9. 21-Mercapto-3α-hydroxy-D-homo-5α-pregnane-11,20-dione, a compound of claim 1.

10. 2β,21-Diethoxy-3α-hydroxy-D-homo-5α-pregnan-20-one, a compound of claim 1.

11. D-Homo-19-nor-5α-pregnane-3,20-dione, a compound of claim 1.

12. D-Homo-19-nor-5β-pregnane-3,20-dione, a compound of claim 1.

13. 3β-Hydroxy-D-homo-19-nor-5α-pregnan-20-one, a compound of claim 1.

14. 3α-Hydroxy-D-homo-19-nor-5β-pregnan-20-one, a compound of claim 1.

15. 3α-Hydroxy-D-homo-19-nor-5α-pregnan-20-one, a compound of claim 1.

16. 3β-Hydroxy-D-homo-19-nor-5β-pregnan-20-one, a compound of claim 1.

17. 3α-Hydroxy-18-methyl-D-homo-19-nor-5β-pregnan-20-one, a compound of claim 1.

18. 11α-Hydroxy-D-homo-19-nor-5α-pregnane-3,20-dione, a compound of claim 1.

19. 11α-Hydroxy-D-homo-19-nor-5β-pregnane-3,20-dione, a compound of claim 1.

20. D-Homo-19-nor-5β-pregnane-3,11,20-trione, a compound of claim 1.

21. 3α-Hydroxy-D-homo-19-nor-5β-pregnane-11,20-dione, a compound of claim 1.

22. 3β-Hydroxy-D-homo-19-nor-5β-pregnane-11,20-dione, a compound of claim 1.

23. D-Homo-19-nor-5α-pregnane-3,11,20-trione, a compound of claim 1.

24. 3β-Hydroxy-D-homo-19-nor-5α-pregnane-11,20-dione, a compound of claim 1.

25. 3α-Hydroxy-D-homo-19-nor-5α-pregnane-11,20-dione, a compound of claim 1.

26. 2β-Ethoxy-3α-hydroxy-D-homo-5α-pregnane-11,20-dione, a compound of claim 1.

27. 3β-Hydroxy-18-methyl-D-homo-19-nor-5α-pregnan-20-one, a compound of claim 1.

28. A compound of claim 1, wherein $R_2$ is oxygen.

29. A compound of claim 1, wherein $R_2$ is

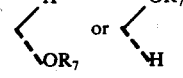

30. A compound of claim 1, wherein $R_4$ is oxygen.

31. A compound of claim 1, wherein $R_4$ is two hydrogens.

32. A compound of claim 1, wherein $R_4$ is

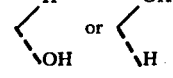

33. A compound of claim 1, wherein the 5-hydrogen is in the α-configuration.

34. A compound of claim 1, wherein the 5-hydrogen is in the β-configuration.

35. A pharmaceutical composition comprising a narcotic-anesthetic amount per unit dosage of a compound of claim 1, in admixture with a pharmaceutically acceptable carrier.

36. A method for inducing anesthesia or narcosis in human and veterinary medicine comprising administering to a patient a narcotic-anesthetic unit dosage of a compound of claim 1, in admixture with a pharmaceutically acceptable carrier.

37. The method of claim 36, wherein the unit dosage is 0.2 - 2 mg./kg. of body weight administered intravenously.